United States Patent [19]

Dabroski

[11] Patent Number: 4,963,139
[45] Date of Patent: Oct. 16, 1990

[54] ABSORBENT BODY HAVING HYDROPHOBIC INSERT

[75] Inventor: Winifred C. Dabroski, East Brunswick, N.J.

[73] Assignee: McNeil-PPC, Inc., Milltown, N.J.

[21] Appl. No.: 247,479

[22] Filed: Sep. 22, 1988

[51] Int. Cl.$^5$ .............................................. A61F 13/16
[52] U.S. Cl. .................................. 604/378; 604/385.1
[58] Field of Search ............... 604/378, 358, 379, 380, 604/381, 385.1

[56] References Cited

U.S. PATENT DOCUMENTS 4,578,066  3/1986  O'Connor ........................... 604/366
4,699,619 10/1987  Bernardin ........................... 604/378
4,813,944  3/1989  Haney et al. ....................... 604/358

FOREIGN PATENT DOCUMENTS 1164020  2/1964  Fed. Rep. of Germany ...... 604/378
0885978  1/1962  United Kingdom ................ 604/378

Primary Examiner—Alan W. Cannon
Assistant Examiner—Natalie Paul

[57] ABSTRACT

A body for absorbing and retaining body fluid is provided containing a fluid repellent insert which substantially separates layers of absorbent material along the longitudinal sides of the absorbent layers so as to prevent leakage of body fluid along the longitudinal sides.

15 Claims, 3 Drawing Sheets

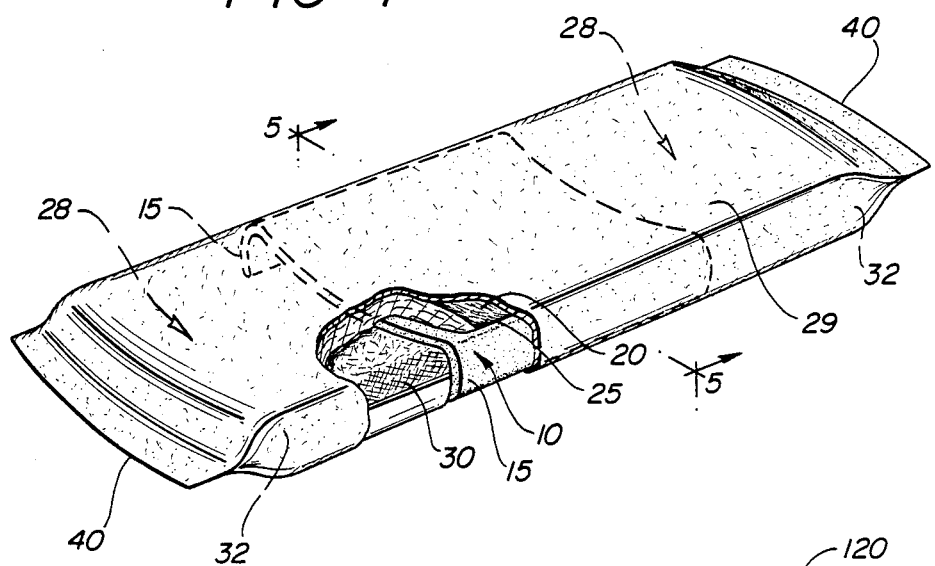
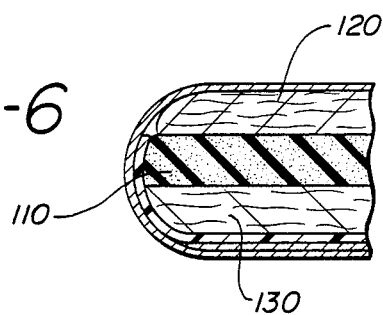
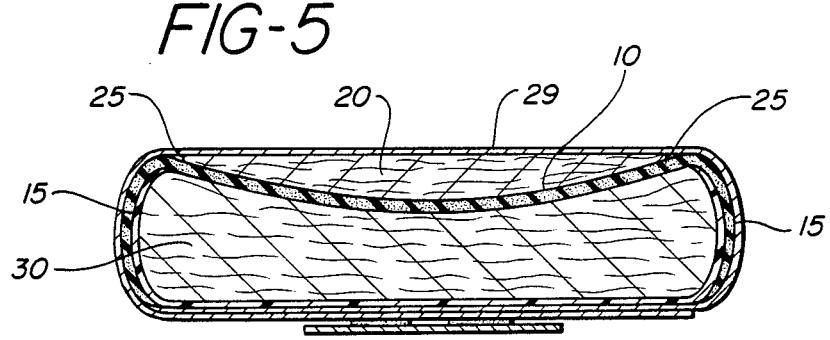

ABSORBENT BODY HAVING HYDROPHOBIC INSERT

BACKGROUND OF THE INVENTION

This invention relates to providing an article for absorbing body fluids. More particularly, this invention relates to an absorbent pad for use in such products as sanitary napkins, panty liners, diapers and the like.

In general, such products comprise one or more layers of a core of hydrophilic material such as wood pulp, rayon tissue or the like. The hydrophilic material, generally fibrous in form, is provided as a pad having a rectangular or oblong shape or in some cases, a shape designed to fit the anatomy of the wearer more closely. Such products may also be designed to have wings or flaps, which extend transversely from the product and serve to protect the wearer's panty from becoming stained due to the tendency for body fluid to flow over the sides of the napkin. The pad is usually provided with an enveloping cover pervious to body fluids on the side of the pad which is to be placed against the body and impervious to such fluids on the side facing away from the body. The object of such a body fluid impervious cover is, of course, to protect the clothing from staining and wetting.

In general, such products have satisfactorily performed their function of absorbing and retaining body fluids and preventing staining and wetting of the wearer's clothing. When the product is properly placed and retained by the wearer in its intended position, body fluid is directed at or near the center of the product and is distributed, by means of liquid wicking, throughout the absorbent medium. However, in a significant number of cases, the product is misplaced, either by the wearer when she initially places the product, or by her activities. Under these circumstances, body fluid will strike the pad off-center and closer to the peripheral edges of the pad. This off-center deposition of body fluid is believed to be the cause of a significant number of failures associated with the use of these products, i.e., the staining and wetting the clothing of the wearer by body fluid. Such failures are known as "side failures".

Even when the product has not been misplaced by the wearer, there are a significant number of failures at the sides of the product. Flow through the absorbent medium after deposition of body fluid is both lateral and longitudinal. Because the distance between the sides of the product is relatively small, fluid can travel laterally and cause side failure quickly.

In the past, there have been efforts to direct the flow of body fluid using baffles or densified sheets. For example, U.S. Pat. No. 3,375,827 (Bletzinger et al.) describes a flow control element located on the body facing side of a main absorbent element of a sanitary napkin. Bletzinger et al. describe the flow control element as a compressed strip of absorbent material of smaller dimension in length and width than the main absorbent element. However, the flow control element rests directly on top of the absorbent core. Thus, the fluid flows radially around and through the flow control element to the core. The fluid, therefore, can flow transversely to the sides of the pad as well as longitudinally, causing side failure.

U.S. Pat. No. 3,612,054 (Matsuda) describes a sanitary napkin having three layers of absorbent material and barrier sheets of liquid repellent material interposed between the layers. Although the barrier sheets are intended to utilize the full capacity of the absorbent layers, they do not address the problem of side failure. Fluid is able to leak throughout the absorbent layers and out the sides of the napkin.

U.S. Pat. No. 4,282,874 (Mesek) describes a diaper having a densified layer. The densified layer is intended to provide a "wickability" gradient which rapidly transmits fluid away from the body-facing layer without permitting it to flow back toward the body. Mesek does not, however, address the problem of preventing leakage at the sides of an absorbent article.

Thus, it is an object of this invention to provide an absorbent article which substantially prevents the flow of body fluid to the sides of the article so as to limit or prevent side failure.

It is another object of this invention to provide an absorbent article such as a sanitary napkin which is capable of directing flow of body fluid along the longitudinal axis of the article.

Yet another object of this invention is to provide an absorbent product in which a large proportion of the absorbent capacity is utilized.

SUMMARY OF THE INVENTION

In accordance with the principles of the present invention, an absorbent product is provided which directs fluid flow along the longitudinal direction of the product and substantially limits or prevents side failure by substantially preventing the flow of fluid around the longitudinal edges of the product. In the absorbent product of this invention, a fluid repellent layer substantially prevents contact between absorbent layers along the longitudinal edges of the product by separating the absorbant layers along their longitudinal edges. The fluid repellent layer permits contact between the top layer and an absorbent layer below the fluid repellent layer at the longitudinal ends of the product. Without an outlet for the fluid at the longitudinal edges, the fluid flows along the longitudinal axis of the absorbent product toward the ends of the product, and is absorbed into one or more bottom reservoir layers.

An absorbent product according to this invention has:

(a) a fluid permeable cover with a body contacting surface;

(b) a first absorbent layer subjacent the cover having oppositely disposed longitudinal edges, a body facing side and a garment facing side;

(c) a fluid repellent layer underlying the first absorbent layer, the width of which is approximately the same as or greater than that of the first absorbent element and the length of which is approximately equal to or less than that of the first absorbent layer;

(d) a second absorbent layer subjacent the fluid repellent layer, the length of which is greater than that of the fluid repellent layer and equal to or greater than that of the first absorbent layer and the width of which is less than, equal to or greater than that of the first absorbent layer.

The longitudinal edges of the first and second absorbent layers should be separated along a substantial portion of their length.

When body fluid is applied to the absorbent products of this invention, the fluid flows into the first absorbent layer and, being prevented from flowing transversely across the product, must flow toward the ends of the product along the longitudinal axis, around the ends of the fluid repellent layer and into the second absorbent layer.

The first and second and additional absorbent layers may be composed of a variety of materials, including wood cellulose fibers, wood pulp, regenerated cellulose or cotton fibers, rayon or other synthetic fibers and/or other materials known to those of skill in the art to be able to absorb and retain fluids. The absorbent layers are preferably composed of wood pulp, as it has an extremely high capacity for absorbing and retaining fluids. The absorbent layers may be rectangular or shaped in a desired manner.

The top and bottom absorbent layers may be made of materials having different degrees of absorbency and retention. For example, the bottom layer may be relatively more absorbent than the top layer. This absorbency differential would promote the transfer and flow of fluid from the top layer to the bottom layer.

The fluid repellent layer should have properties which render it repellent to fluid relative to the absorbent layers. Thus, it need not be composed only of foams or other materials which are considered by those in the art to be "hydrophobic", i.e. which does not absorb or adsorb fluid. In fact, it may be composed of an absorbent material, as long as the material is less absorbent than the absorbent layers. Preferably, the fluid repellent layer is a polymeric foam. Not only is such a foam fluid repellent, but it provides resiliency to the sanitary napkin, allowing it to retain its shape and aid in maintaining good contact between the absorbent product and the user's body. For example, the fluid repellent layer may be a urethane foam, a polyethylene foam, a styrene foam, a rubber foam, an aminoether foam, or the like. More preferably, the foam is a urethane foam. The foam should be perceived to be comfortable by the wearer. It should also be somewhat resilient in order to protect the pad from being crushed or mangled during use. Preferably, the foam density should be between about .035 gm and about .320 gm. The stiffness of the foam as measured on a Gurley Stiffness Tester (manufactured by W. and L.E. Gurley of Troy, N.Y. as described in U.S. Pat. No. 4,354,901, issued Oct. 19, 1982 to Kopolow) should be between about 1 and 9. More preferably, it should be between about 2 and 6.

BRIEF DESCRIPTION OF THE DRAWINGS

FIG. 4 is a perspective view of one of the preferred embodiments of the absorbent products of this invention.

FIG. 5 is a transverse cross-sectional view of the product depicted in FIG. 4 along the line 5—5.

FIG. 6 is a partial cross-sectional view of another preferred embodiment of the products of this invention.

FIGS. 1–3 represent a preferred embodiment of a sanitary napkin according to this invention which has very short side projections, or "winglets" formed by fluid repellent layer side projections. Bottom absorbent layer 230, which may be composed of wood pulp fluff is coterminous with top absorbent layer 220 which may also be made of wood pulp fluff. Fluid repellent layer 210 is superimposed over bottom absorbent layer 230 and extends on either side beyond the width of the top and bottom absorbent layers. The side projections of fluid repellent layer 210 not only protect against side failure by preventing the contact between the absorbent layers at the side or longitudinal edges, but they provide extra protection for the wearer's undergarments. They also provide resilient edges which aid in preventing chafing and irritation of the legs when contacting the side wings.

FIGS. 4 and 5 depict one of the preferred embodiments of the absorbent body of this invention. Bottom absorbent layer 30 may be composed of a wood pulp fluff pad. Fluid repellent layer 10 is superimposed over bottom absorbent layer 30. Fluid repellent layer 10 also has side projections 15 which may be bent away from the body-facing side of the pad along the side and around the longitudinal edges of absorbent layer 30 in the form of a "saddle." A smaller absorbent layer 20 is superimposed over absorbent layer 30, and has the same width, but a smaller length than absorbent layer 30. Fluid which impinges top absorbent layer 20 and which flows radially to longitudinal edges 25 of absorbent layer 20 is prevented from flowing beyond longitudinal edges 25 of absorbent layer 20 by fluid repellent layer 10. The fluid then seeks to flow in the longitudinal direction to transverse ends 28 of absorbent layer 20. Transverse ends 28 of absorbent layer 20 contact the transverse ends 32 of absorbent layer 30 and permit the transfer of fluid from layer 20 to layer 30. The entire structure is wrapped with a cover layer 29 and may be flange sealed at the longitudinal ends 40 of the product.

FIG. 6 depicts another preferred embodiment of the product of this invention. Bottom absorbent layer 130 and top absorbent layer 120 are coterminous. However, fluid repellent layer 110, having approximately the same width as absorbent layers 120 and 130, prevents the contacts between absorbent layers 120 and 130 at the longitudinal edges. Fluid striking top absorbent layer 120 cannot flow beyong the edges from the top most layer to bottom absorbent layer 130 due to the gap created by the fluid repellent layer. The fluid must flow along the longitudinal axis toward the ends of the absorbent layers.

FIGS. 7 and 8 depict photographs of a sanitary napkin made in accordance with this invention. The fluid repellent layer of the napkin has winglet side projections. Ersatz menstrual fluid has been deposited on the napkin and the flow patterns examined. FIG. 7 demonstrates that the portion of the top repellent layer which is coterminous with the fluid repellent layer is saturated with fluid. FIG. 8 demonstrates that the fluid flows preferentially over the longitudinal ends of the fluid repellent layer into the bottom absorbent layer rather than over the sides, which would cause side failure.

Figure 1:
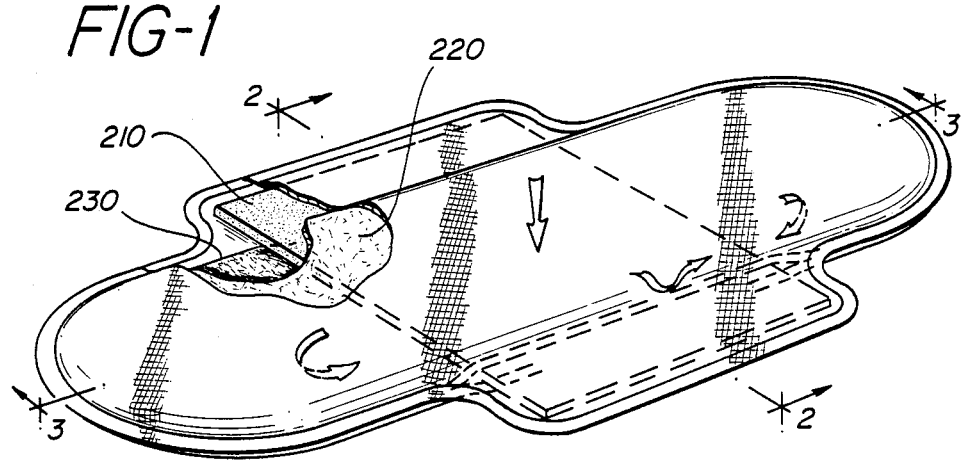
FIG. 1 is a perspective view of one of the preferred embodiments of the absorbent products of this invention.
Figure 2:
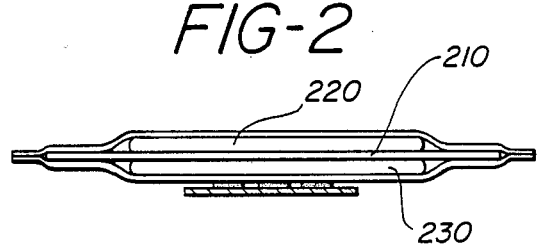
FIG. 2 is a transverse cross-sectional view of the embodiment depicted in FIG. 1 along the line 2—2.
Figure 3:
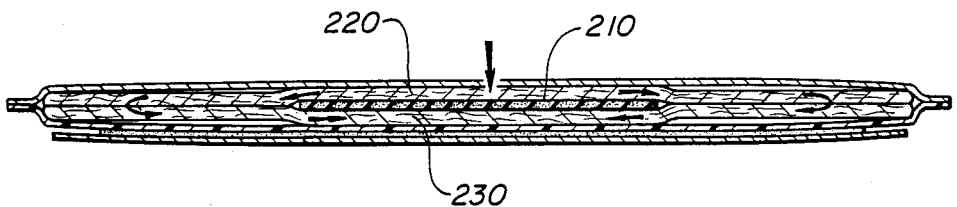
FIG. 3 is a longitudinal cross-sectional view of the embodiment depicted in FIG. 1 along the line 3—3.
Figure 7:
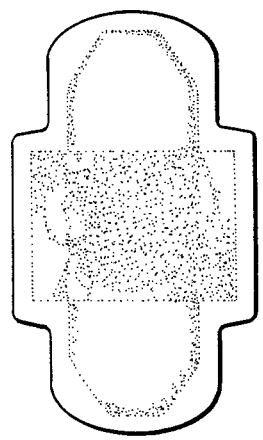
FIG. 7 is an illustration of a preferred embodiment of the products of this invention after in vivo use.
Figure 8:
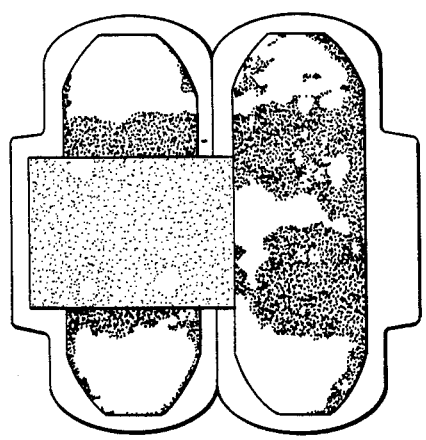
FIG. 8 is an illustration of the napkin depicted in FIG. 7 wherein the layers of the product have been opened to reveal the pattern of deposition of body fluid.

The effectiveness of using the products of this invention is demonstrated by the following examples. Of course, these examples are not intended to limit the scope of the invention in any way, but merely serve to illustrate the products of this invention and the use thereof.

EXAMPLE 1

A sanitary napkin was constructed using an embossed polypropylene backing having a triple row of Fuller 1940W hot melt positioning adhesive (a styrene-ethylenebutadiene-styrene block copolymer resin and oil available from H. P. Fuller Co.), two compressed light weight pulp pads having a total weight of 5.0 g, a fluid repellent layer made of General Foam P3800 (a urethane foam film available from General Foam Co.) approximately 3 inches long × 4 inches wide × ⅛ inch deep located on top of the compressed pulp pads, and a fluffy layer of pulp about 7.5 inches long × 2.6 inches wide on top of the foam. The product was covered with an apertured film made of coextruded polyethylene and ethylvinylacetate described in U.S. Pat. No. 4,690,679 using a spray. The cover was flange sealed to the polypropylene backing. The napkin was formed with small side panel projections each having a width of about 0.7 inches.

EXAMPLE 2

A sanitary napkin was formed using a pulp pad about 3 inches long × 3-½ inches wide × 7-½ inches thick. A ⅛ inch thick, 3-½ inch wide, 3 inch long urethane foam pad was glued to the pulp pad using 331581 Adhesive Polyvinylacetate, available from National Starch Co. The sides of the foam pad extended slightly beyond the sides of the pulp pad. Over the foam pad was glued a smaller pulp pad, 6-¼ inches long × 2 inches wide × ¼ inch thick. The sanitary napkin was overwrapped with a fibrous dry cover having 165 apertures/square inch (described in copending application Ser. No. 869,156). A spray adhesive, Fuller 1940W (See Example 1), was used to adhere the cover to the pad. A polyethylene boat 3-½ inches in width was placed under the bottom, larger pulp pad. The process of overwrapping the napkin pulled the side extensions of the foam pad around the sides of the bottom pulp pad, forming a "saddle".

EXAMPLE 3

A sanitary napkin was made in accordance with Example 2, with the exception that a fluid repellent layer composed of Hollofil ™ brand polyester fibers (available from E.I. duPont de Nemours Co.) 3 inches long by 3 inches wide was used; 2-½ inches in the center of the fluid repellent layer was compressed and ¼ inch was left uncompressed and allowed to hang over the sides of the polyethylene boat.

EXAMPLE 4

A sanitary napkin was formed using a pulp pad having dimensions of 7-½ inches long × 3 inches wide. Over the pulp pad was placed a ⅛ inch thick × 3 inches long × 4 inches wide General Foam urethane pad which was to act as a fluid repellent layer. A smaller pulp pad was glued over the foam layer. A 0.001 inch thick white embossed polyethylene backing was placed under the napkin and flange sealed to a coextruded apertured film cover using cover spray adhesive.

EXAMPLE 5

A sanitary napkin was made in accordance with Example 2, with the exception that the fluid repellent layer was a blue embossed layer of polypropylene 3 inches long × 3-½ inches wide × ⅛ inch thick.

EXAMPLE 6

A sanitary napkin was made using a light weight pulp pad compressed in the center and a urethane foam pad 3 inches wide × 1-¾ inches long × ⅜ inches thick which was laid into the compressed area of the pulp pad. A smaller pulp pad was placed over the foam. The foam was glued to both pulp pads. The pad was overwrapped with a fibrous dry cover using cover spray.

The following Examples are illustrative of in vivo menstrual use of the products of this invention.

EXAMPLE A

Menstruating women were given a number of sanitary napkins for alternative testing. Twenty women each received six sanitary napkins made in accordance with Example 1 and six Regular ALWAYS ™ brand Regular Maxipad sanitary napkins commercially available from The Procter & Gamble Company. The pads were numbered consecutively and the women instructed to use the pads in consecutive numerical order. The pads were to be worn for six hours or until failure, whichever was first. Failure was defined as leakage of menstrual fluid from the side of a napkin, from the ends of a napkin or from a combination of the sides and the ends. Of the Example 1 sanitary napkins, six of the forty-eight napkins used exhibited a failure, or 12.5%. Fourteen of the fifty-one ALWAYS ™ maxipads used resulted in a failure, or 27.5%.

EXAMPLE B

An alternate use test was conducted in accordance with the procedure outlined in Example A, with the exception that the sanitary napkins of Examples 2 and 3 were used in place of the napkins described in Example A. The use of the napkins of Example 2 resulted in five failures out of forty-one napkins used, or 12.2% failures. The use of the napkins of Example 3 resulted in nine failures out of fifty-two napkins used, or 17.31%.

EXAMPLE C

An alternate use test was conducted in accordance with the procedure outlined in Example A, with the exception that the sanitary napkins of Example 4 were used in alternation with ALWAYS ™ Regular Maxipads available from Procter & Gamble. The use of the napkins of Example 4 resulted in eight failures out of fifty-four napkins, or 14.8% failures. The use of ALWAYS ™ Regular Maxipads, in comparison with the use of the napkins made according to this invention, resulted in twenty-four failures out of fifty-five napkins used, or 43.64% failures. This indicates that the napkins made in accordance with this invention are more effective in preventing failures than the commercially available ALWAYS ™ Regular Maxipad product.

EXAMPLE D

An alternate use test was conducted in accordance with the procedure outlined in Example A, with the exception that the sanitary napkins of Examples 2 and 5 were used in place of the napkins described in Example A. The use of the napkins of Example 2 resulted in 0 failures out of fourteen napkins used, or 0% failures. The use of the napkins made in accordance with Example 5 resulted in one failure out of sixteen napkins used, or 6.25% failure.

EXAMPLE E

An alternate use test was conducted in accordance with the procedure outlined in Example A, with the exception that the sanitary napkins of Example 6 were used in place of the napkins described in Example A with ALWAYS TM Brand Regular "New-Longer" Maxipads. Use of the napkins of Example 6 resulted in ten failures out of sixty-seven napkins used, or 14.93% failures. The alternatively-used napkins, ALWAYS TM Brand Longer napkins resulted in thirty-six failures out of sixty-eight napkins used, or 52.94% failures. This comparison demonstrates the unexpectedly superior performance of the products of Applicant's invention in comparison with napkins lacking a fluid repellent layer in accordance with this invention.

EXAMPLE F

(Non-working Example)

In this Example, an alternate use test was conducted in accordance with the procedure outlined in Example A, with the exception that sanitary napkins in which a foam fluid repellent layer was inserted which was narrower than the absorbent layers were used in comparison with STAYFREE TM Brand Maxi Pads. The use of the napkins of Example 7 resulted in five failures out of sixteen napkins used, or 31.25% failures. The use of the STAYFREE TM Brand Maxi Pads resulted in six failures out of eighteen napkins used, or 33.33% failures. The demonstrates that mere insertion of a foam fluid repellent layer is insufficient to prevent or substantially reduce the number of failures resulting from the use of sanitary napkins.

What is claimed is:

1. An absorbent article having oppositely disposed ends and longitudinal edges, comprising:
   (a) a fluid permeable cover with a body contacting surface;
   (b) a first absorbent layer subjacent to said cover having oppositely disposed longitudinal edges, and oppositely disposed transverse edges, a body facing side and a garment facing side;
   (c) a fluid repellent layer underlying said first absorbent layer having oppositely disposed longitudinal edges and oppositely disposed transverse edges, the distance between said longitudinal edges being substantially the same as or greater than that of the first absorbent element and the distance between said transverse edges being substantially equal to or less than that of said first absorbent element; a second absorbent element having oppositely disposed longitudinal edges and oppositely disposed transverse edges, underlying said fluid repellent layer the distance between said transverse edges being greater than that of said fluid repellent layer; whereby in use, said first and said second absorbent layers are substantially separated a distance along their longitudinal edges such that fluid striking said first absorbent layer is substantially prevented from flowing around the longitudinal edges and substantially flows along the longitudinal direction of the absorbent article toward the transverse edges into said second absorbent element.

2. An absorbent article according to claim 1, wherein the distance between the longitudinal edges of the fluid repellent layer is greater than said distances of said first and second absorbent elements.

3. An absorbent article according to claim 1, wherein the distance between the longitudinal edges of said second absorbent element is greater than that of the first absorbent layer.

4. An absorbent article according to claim 1, wherein the distance between the longitudinal edges of said second absorbent element is substantially the same as that of the fluid repellent layer.

5. An absorbent article according to claim 2, wherein said fluid repellent layer comprises a material selected from the group consisting of fibrous materials and polymeric foams.

6. An absorbent article according to claim 5, wherein said fluid repellent layer comprises fibrous materials.

7. An absorbent article according to claim 6, wherein said fibrous materials are selected from the group consisting of rayon fibers which have been treated with a repellent material; bicomponent polyester fibers treated with a repellent material; and polyethylene fibers.

8. An absorbent article according to claim 5 wherein said fluid repellent layer comprises a material selected from the group consisting or urethane foam, styrene foam, rubber foam, and aminoether foam.

9. An absorbent article having oppositely disposed ends and longitudinal edges, comprising:
   (a) a fluid permeable cover with a body contacting surface;
   (b) a first absorbent layer subjacent to said cover having oppositely disposed longitudinal edges, and oppositely disposed transverse edges, a body facing side and a garment facing side;
   (c) a fluid repellent layer underlying said first absorbent layer having oppositely disposed longitudinal edges and oppositely disposed transverse edges, the distance between said longitudinal edges being substantially the same as or greater than that of the first absorbent element and the distance between said transverse edges being substantially equal to or less than that of said first absorbent element; a second absorbent element having oppositely disposed longitudinal edges and oppositely disposed transverse edges, underlying said fluid repellent layer the distance between said transverse edges being greater than that of said fluid repellent layer; whereby said first and said second absorbent layers are substantially separated a distance along their longitudinal edges such that fluid striking said first absorbent layer is substantially prevented from flowing around the longitudinal edges and substantially flows along the longitudinal direction of the absorbent article into said second absorbent element, wherein said second absorbent layer is more absorbent than said first absorbent layer.

10. An absorbent article according to claim 1, wherein said first and second absorbent layers comprise wood pulp fluff.

11. An absorbent article according to claim 1, wherein the distance between the longitudinal edges of said fluid repellent layer is substantially the same as those of the first and second absorbent layers.

12. An absorbent article according to claim 2, wherein said fluid repellent layer protrudes beyond the longitudinal edges of said second absorbent layer and is capable of being wrapped toward the garment facing side of the absorbent article.

13. An absorbent article according to claim 4 wherein said fluid repellent layer comprises a foam having a Gurley Stiffness of between about 1 gm and about 9 gm.

14. An absorbent article according to claim 13 wherein said Gurley Stiffness is between about 2 gm and about 6 gm.

15. An absorbent article according to claim 13 wherein the density of said foam is between about 0.15 and 0.15 g/cc.

* * * * *